United States Patent

Doi et al.

(10) Patent No.: US 6,348,598 B1
(45) Date of Patent: Feb. 19, 2002

(54) N-OXYL COMPOUNDS, PROCESS FOR THE PREPARATION THEREOF, AND PROCESS FOR INHIBITING THE POLYMERIZATION OF VINYL MONOMERS WITH THE SAME

(75) Inventors: Junichi Doi; Hiroshi Sonobe, both of Hiroshima; Akio Tani, Ishikawa; Shinji Suzuki; Masafumi Akehi, both of Osaka, all of (JP)

(73) Assignees: Mitsubishi Rayon Co., Ltd., Tokyo; Osaka Organic Chemical Ind. Co., Ltd., Osaka, both of (JP)

( * ) Notice: Subject to any disclaimer, the term of this patent is extended or adjusted under 35 U.S.C. 154(b) by 0 days.

(21) Appl. No.: 09/554,072

(22) PCT Filed: Nov. 12, 1998

(86) PCT No.: PCT/JP98/05085

§ 371 Date: May 11, 2000

§ 102(e) Date: May 11, 2000

(87) PCT Pub. No.: WO99/24402

PCT Pub. Date: May 20, 1999

(30) Foreign Application Priority Data

Nov. 21, 1997 (JP) ................................ 9-310573

(51) Int. Cl.$^7$ ..................... C07C 211/94; C07D 57/04; C07D 69/52
(52) U.S. Cl. .................. 546/242; 560/205; 562/598
(58) Field of Search .................. 546/242; 560/205; 562/598

(56) References Cited

PUBLICATIONS

Marinovic et al, Polymer, vol. 32, No. 14, p.2519–2522 (1991).*

\* cited by examiner

*Primary Examiner*—Bernard Dentz
(74) *Attorney, Agent, or Firm*—Oblon, Spivak, McClelland, Maier & Neustadt, P.C.

(57) ABSTRACT

Disclosed are novel N-oxyl compounds of the following formula (1).

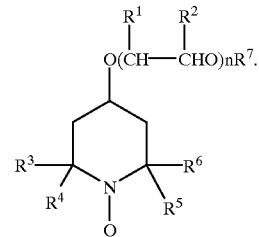

(1)

wherein n is an integer of 1 to 18; $R^1$ and $R^2$ are each hydrogen or methyl, but at least one of them is hydrogen; $R^3$, $R^4$, $R^5$ and $R^6$ are each a straight-chain or branched alkyl group; and $R^7$ is hydrogen or (meth) acryloyl. When these compounds are added to vinyl monomers such as α,β-unsaturated carboxylic acids and esters thereof, they exhibit a satisfactory polymerization-inhibiting effect even at low contents and even at elevated temperatures.

12 Claims, 2 Drawing Sheets

N-OXYL COMPOUNDS, PROCESS FOR THE PREPARATION THEREOF, AND PROCESS FOR INHIBITING THE POLYMERIZATION OF VINYL MONOMERS WITH THE SAME

This application is a 371 of PCT/JP98/05085 filed Nov. 12, 1998.

TECHNICAL FIELD

This invention relates to novel N-oxyl compounds, mixtures of such N-oxyl compounds, a process for preparing them, and a method for inhibiting the polymerization of vinyl monomers, such as α,β-unsaturated carboxylic acids and esters thereof, by using them.

BACKGROUND ART

α,β-Unsaturated carboxylic acids and esters thereof, which are typical of vinyl monomers, are compounds having a wide variety of uses as monomers for the production of various polymers and copolymers. However, since they have the property of being very easily polymerized, polymerization troubles due to causative factors such as heat and light may frequently occur during the course of their production, storage, transport and the like. Especially in the production of α,β-unsaturated carboxylic acids and esters thereof, they are exposed to high temperatures above 100° C. and hence tend to cause the trouble of forming a popcorn polymer in the liquid and vapor phases.

In order to prevent the above-described polymerization troubles occurring in α,β-unsaturated carboxylic acids and esters thereof, attempts have been made to inhibit their polymerization by using various polymerization inhibitors. Such polymerization inhibitors include, for example, heteroaromatic compounds such as phenothiazine; phenols such as hydroquinone and hydroquinone monomethyl ether; and aromatic amines such as N,N'-di-2-naphthyl-p-phenylenediamine [Nonflex F (trade name), manufactured by Seiko Chemical Co., Ltd.; hereinafter abbreviated as "AF"], N-phenyl-N'-(1,3-dimethylbutyl)-p-phenylenediamine [Nocrak 6C (trade name), manufactured by Ouchishinko Chemical Industrial Co., Ltd.; hereinafter abbreviated as "6C"] and N,N'-diphenyl-p-phenylenediamine [Nonflex H (trade name), manufactured by Seiko Chemical Co., Ltd.]. Moreover, Japanese Patent Laid-Open Nos. 320205/'93 and 320217/'93 disclose a method using an N-oxyl compound of the following formula (2) alone or in combination with other polymerization inhibitors.

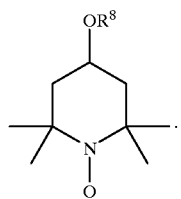

(2)

wherein $R^8$ represents hydrogen, an alkyl group or an acyl group.

However, under high-temperature conditions employed for the purpose of reaction and purification by distillation in processes for the production of α,β-unsaturated carboxylic acids and esters thereof, conventional polymerization inhibitors fail to exhibit a satisfactory polymerization-inhibiting effect. Consequently, these polymerization inhibitors need to be added in large amounts and hence have a problem from the viewpoint of industrial use. Moreover, although the N-oxyl compounds of formula (2) in which $R^8$ is hydrogen or an alkyl group have an excellent polymerization-inhibiting ability even when used in small amounts, the actually known compounds of this type are limited to those in which $R^8$ is hydrogen, methyl or ethyl. These compounds have relatively low boiling points or sublimation temperatures which are close to the boiling points of α,β-unsaturated carboxylic acids and esters thereof, and hence involve the problem that, during the purification of α,β-unsaturated carboxylic acids and esters thereof by distillation, they are distilled out together with the product to cause a coloration thereof. On the other hand, the N-oxyl compounds of formula (2) in which $R^8$ is an acyl group have sufficiently high boiling points or sublimation temperatures. However, during use, they may be converted to compounds having low boiling points or sublimation temperatures and may eventually be distilled out together with the product. As an example of this phenomenon, when an N-oxyl compound of formula (2) is used as a polymerization inhibitor for the ester exchange reaction between methyl (meth)acrylate and an alcohol, the polymerization inhibitor itself may undergo an ester exchange reaction to form a compound containing a (meth)acryloyl group as $R^8$ and hence having a low boiling point or sublimation temperature, and may eventually be distilled out together with the product to cause a coloration thereof.

DISCLOSURE OF THE INVENTION

An object of the present invention is to provide novel N-oxyl compounds and a process for preparing them.

Another object of the present invention is to provide a polymerization inhibition method which, when employed in processes for the production of vinyl monomers such as α,β-unsaturated carboxylic acids and esters thereof, causes little coloration of the product and does not require a large amount of polymerization inhibitor.

That is, the present invention relates to an N-oxyl compound of the following formula (1).

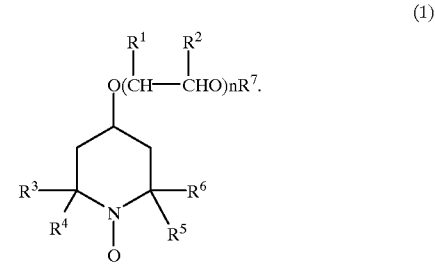

(1)

wherein n is an integer of 1 to 18; $R^1$ and $R^2$ are each hydrogen or methyl, but at least one of them is hydrogen; $R^3$, $R^4$, $R^5$ and $R^6$ are each a straight-chain or branched alkyl group; and $R^7$ is hydrogen or (meth)acryloyl.

Moreover, the present invention also relates to a process for the preparation of an N-oxyl compound of formula (1) which comprises the steps of effecting the addition of ethylene oxide and/or propylene oxide to a 4-hydroxy-2,2,6,6-tetraalkylpiperidine-N-oxyl, and optionally esterifying the resulting product with a (meth)acryloyl-containing compound.

Furthermore, the present invention also relates to a polymerization inhibition method wherein an N-oxyl compound of formula (1) or a mixture of such N-oxyl compounds is used as a polymerization inhibitor for vinyl monomers.

BEST MODE FOR CARRYING OUT THE INVENTION

Figure 1:
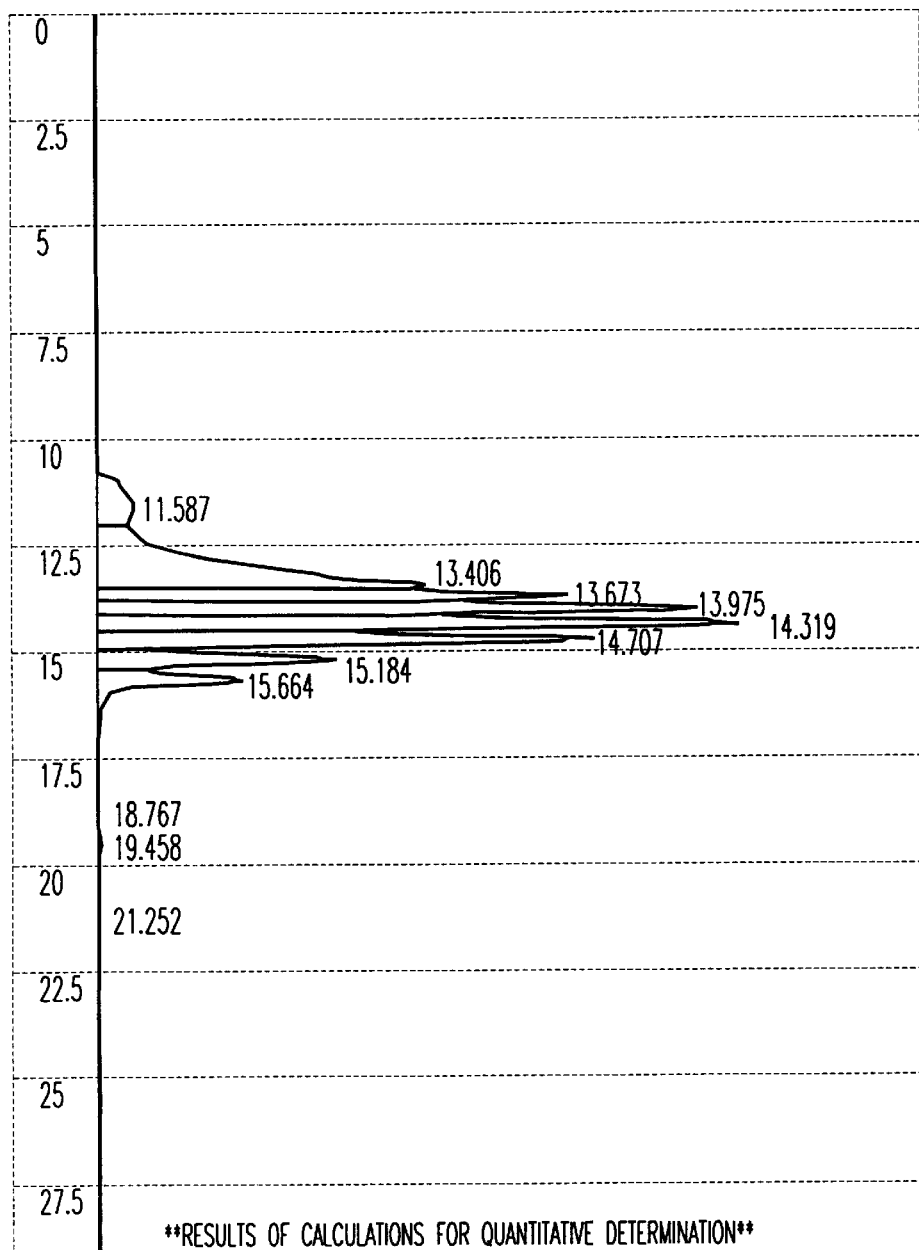
FIGS. 1 and 2 are graphs showing the results of analysis by high-performance liquid chromatography for the N-oxyl compounds (IB and IE) of the present invention which were obtained in Examples 1 and 2, respectively.

The N-oxyl compounds of the present invention are compounds represented by formula (1). In this formula, each of $R^3$, $R^4$, $R^5$ and $R^6$ is a straight-chain or branched alkyl group. However, each of $R^3$, $R^4$, $R^5$ and $R^6$ is preferably a straight-chain alkyl group of 1 to 4 carbon atoms and more preferably methyl.

Although the N-oxyl compounds of formula (1) in accordance with the present invention may be obtained in the form of a pure compound in which n is an integer of 1 to 18, they are usually obtained as a mixture of two or more N-oxyl compounds having different values of n. In this case, the average value of n per mole of the N-oxyl compounds (hereinafter referred to as the average number of moles added) is suitably in the range of 1 to 14. If the average number of moles added is greater than 14, the molecular weight becomes so great that the weight required to provide the same number of moles will be unduly increased. Moreover, the boiling point or sublimation temperature of the mixture of N-oxyl compounds is raised to such an extent that it cannot be easily used as a polymerization inhibitor. The preferred range of the average number of moles added is from 2 to 10.

The N-oxyl compounds of the present invention in which $R^7$ in formula (1) is hydrogen may be synthesized by effecting the addition reaction of ethylene oxide and/or propylene oxide, for example, to 4-hydroxy-2,2,6,6-tetramethylpiperidine-N-oxyl.

According to one exemplary procedure for effecting the addition reaction of ethylene oxide, a four-necked flask fitted with a stirrer, a thermometer and a brine condenser is charged with 4-hydroxy-2,2,6,6-tetramethylpiperidine-N-oxyl, a solvent and a catalyst. Then, ethylene oxide is introduced into the system by blowing it in at such a rate that it is not refluxed in the lower part of the brine condenser. After a predetermined amount of ethylene oxide has been blown in, the stirring is continued until the disappearance of 4-hydroxy-2,2,6,6-tetramethylpiperidine-N-oxyl used as a starting material is confirmed. After the reaction is stopped, the reaction mixture is stirred under reduced pressure to remove any unreacted ethylene oxide. Consequently, an N-oxyl compound of formula (1), or a mixture of such N-oxyl compounds, is obtained as residue. Similarly, the addition reaction of propylene oxide may be carried out by controlling the dropping rate of propylene oxide so that it is not refluxed in the lower part of the brine condenser.

The solvents which can be used for the addition reaction include, for example, halogenated hydrocarbons such as methylene chloride, chloroform, carbon tetrachloride and chlorobenzene; aromatic hydrocarbons such as benzene, toluene, xylene, cumene and ethylbenzene; and ether solvents such as diethyl ether, diisopropyl ether, tetrahydrofuran, tetrahydropyran and dioxane. Among others, aromatic hydrocarbons are preferably used.

As the catalyst for the addition reaction of ethylene oxide and/or propylene oxide, there may be used any of the common polymerization catalysts for ethylene oxide and/or propylene oxide. For example, alkali hydroxides, iron(III) chloride and tin(IV) chloride are preferably used. Among them, iron(III) chloride is especially preferred.

In carrying out the addition reaction of ethylene oxide and/or propylene oxide, it is necessary to add ethylene oxide and/or propylene oxide while maintaining the reaction mixture at such a temperature that they are not refluxed. Specifically, the reaction mixture is maintained at a temperature of −10 to 40° C. and preferably 0 to 30° C. After completion of the addition of ethylene oxide and/or propylene oxide, the reaction is preferably carried out at an elevated temperature of 20 to 50° C. After completion of the reaction, degassing is also preferably carried out at a temperature of 20 to 50° C.

The N-oxyl compounds of the present invention in which $R^7$ in formula (1) is (meth)acryloyl may be synthesized by effecting the addition reaction of ethylene oxide and/or propylene oxide, for example, to 4-hydroxy-2,2,6,6-tetramethylpiperidine-N-oxyl, and subsequently subjecting the resulting product to esterification with (meth)acrylic acid or ester exchange with a (meth)acrylate.

An N-oxyl compound having a given value of n may be obtained by controlling the amount of ethylene oxide and/or propylene oxide added. However, the N-oxyl compound obtained in this manner usually comprises a mixture of two or more N-oxyl compounds having different values of n. If necessary, therefore, pure N-oxyl compounds having a definite value of n can be isolated by purifying the mixture according to such techniques as column chromatography and distillation. For the mixture of N-oxyl compounds obtained by the addition reaction, the average number of moles added can be determined by dividing the number of moles of ethylene oxide and/or propylene oxide added by the number of moles of 4-hydroxy-2,2,6,6-tetramethylpiperidine-N-oxyl converted to the adduct.

The N-oxyl compounds of formula (1) in accordance with the present invention can be used as polymerization inhibitors for preventing the polymerization of vinyl monomers. These polymerization inhibitors have higher boiling points or sublimation temperatures as n is increased. Accordingly, in order to reduce the amount of polymerization inhibitor contaminated into the product in the distillation process, it is preferable to select a polymerization inhibitor having a boiling point or sublimation temperature which is substantially different from the boiling point of the vinyl monomer as the product.

As compared with aromatic amine compounds conventionally used as polymerization inhibitors, the N-oxyl compounds of formula (1) are characterized in that they have excellent solubility in α,β-unsaturated carboxylic acids and esters thereof and in that the equipment and tanks can be easily cleaned after use. For this reason, they are very favorable for industrial use. When, among the N-oxyl compounds of formula (1), those in which $R^7$ is hydrogen are used as polymerization inhibitors in an ester exchange reaction process using methyl (meth)acrylate as a starting material, part or all of them may be converted to compounds in which $R^7$ is (meth)acryloyl. However, there is no problem from a practical point of view because their polymerization-inhibiting ability is comparable to that of the corresponding compounds in which $R^7$ is hydrogen and they do not tend to be distilled out into the product.

The polymerization inhibition method of the present invention can be applied not only to the purpose of polymerization inhibition in processes for the production of vinyl monomers, preferably α,β-unsaturated carboxylic acids and esters thereof, but also to the purpose of polymerization inhibition during storage and transport thereof.

In the polymerization inhibition method of the present invention, at least an N-oxyl compound of formula (1) or a mixture of two or more N-oxyl compounds having different values of n in formula (1) (hereinafter referred to as the mixture of such N-oxyl compounds) is used as a polymerization inhibitor. However, it is a matter of course that other general-purpose polymerization inhibitors may be used in combination therewith. The combined use of other polymerization inhibitors may produce a more excellent polymerization-inhibiting effect owing to the synergistic action of those polymerization inhibitors.

The amount in which the N-oxyl compound of formula (1) or the mixture of such N-oxyl compounds is added may vary according to the process and conditions employed. However, when they are used alone, the amount added is generally in the range of about 1 to 1,000 ppm based on the vinyl monomer whose polymerization is to be inhibited. When they are used in combination with other polymerization inhibitors, it is generally in the range of about 0.5 to 1,000 ppm.

All of the N-oxyl compounds of formula (1) and the mixtures of such N-oxyl compounds have a polymerization-inhibiting effect on vinyl monomers. Accordingly, when these polymerization inhibitors are used, a suitable polymerization inhibitor may be selected with consideration for the boiling point of the vinyl monomer, the operating conditions or the like.

In the practice of the present invention, the N-oxyl compound of formula (1), or the mixture of such N-oxyl compounds, used as a polymerization inhibitor is added to a vinyl monomer either as such or in the form of a solution. Where it is desired to prevent the polymerization of a vinyl monomer within a distillation column, it is common practice to dissolve the polymerization inhibitor, for example, in a substance contained in the distillation system and supply this solution to the top or middle of the distillation column. In this case, if a mixture of two or more N-oxyl compounds having different value of n in formula (1) is used, these compounds have different boiling points and, therefore, are widely distributed within the distillation column as contrasted with a pure compound which is present only in some part of the distillation column. Accordingly, the use of a mixture represents a preferred embodiment in that a polymerization-inhibiting effect on the vinyl monomer is exhibited over a great part of the distillation column.

In the polymerization inhibition method of the present invention, the vinyl monomer containing an N-oxyl compound of the above formula (1) or a mixture of such N-oxyl compounds as a polymerization inhibitor may additionally contain molecular oxygen or air, if necessary, in order to achieve a further enhancement in polymerization-inhibiting effect. This may readily be accomplished by such techniques as air bubbling.

The polymerization inhibition method of the present invention can be applied to vinyl monomers in general, and it can be applied not only to a single vinyl monomer but also to a mixture of two or more vinyl monomers. Moreover, an excellent effect is achieved especially when the polymerization inhibition method of the present invention is applied to α,β-unsaturated carboxylic acids and esters thereof. Useful vinyl monomers include ethylene, propylene, butadiene, styrene, vinyl chloride and the like. Useful α,β-unsaturated carboxylic acids and esters thereof include, for example, acrylic acid, methyl acrylate, ethyl acrylate, n-butyl acrylate, i-butyl acrylate, stearyl acrylate, 2-ethylhexyl acrylate, 2-hydroxyethyl acrylate, 2-hydroxypropyl acrylate, 4-hydroxybutyl acrylate, ethylene glycol diacrylate, glycidyl acrylate, 2-ethoxyethyl acrylate, tetrahydrofurfuryl acrylate, cyclohexyl acrylate, benzyl acrylate, allyl acrylate, t-butyl acrylate, 1,6-hexanediol diacrylate, dimethylaminoethyl acrylate, methacrylic acid, methyl methacrylate, ethyl methacrylate, n-butyl methacrylate, i-butyl methacrylate, stearyl methacrylate, 2-ethylhexyl methacrylate, 2-hydroxyethyl methacrylate, 2-hydroxypropyl methacrylate, ethylene glycol dimethacrylate, glycidyl methacrylate, 2-ethoxyethyl methacrylate, cyclohexyl methacrylate, benzyl methacrylate, allyl methacrylate, t-butyl methacrylate, dimethylaminoethyl methacrylate, phenyl methacrylate, crotonic acid, methyl crotonate, ethyl crotonate, itaconic acid, dimethyl itaconate, methyl α-hydroxyethylacrylate and ethyl α-hydroxyethylacrylate. It is a matter of course that the present invention is not limited thereto.

The present invention is more specifically explained with reference to the following examples and comparative examples. The polymerization inhibitors used therein are designated by the abbreviations shown in Tables 1 and 2. In all of the polymerization inhibitors of formula (1) in which $R^1$, $R^2$ and the average number of moles added (n) are varied as shown in Table 1, $R^3$, $R^4$, $R^5$ and $R^6$ are $CH_3$ and $R^7$ is H.

TABLE 1

| | n, $R^1$ and $R^2$ in compound of general formula (1) | | |
|---|---|---|---|
| Abbreviation | n | $R^1$ | $R^2$ |
| IA | 2 | H | H |
| IB | 6 | H | H |
| IC | 10 | H | H |
| ID | 0 | — | — |
| IE | 3 | One of $R^1$ and $R^2$ is H and the other is $CH_3$ | |
| IF | 6 | One of $R^1$ and $R^2$ is H and the other is $CH_3$ | |
| IG | 10 | One of $R^1$ and $R^2$ is H and the other is $CH_3$ | |

TABLE 2

| Abbreviation | Structural formula of polymerization inhibitor |
|---|---|
| HQ |  |
| MEHQ | 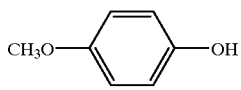 |
| PZ | 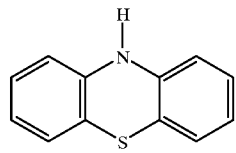 |
| AF | 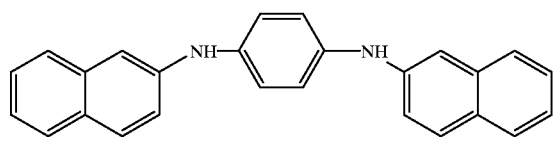 |
| 6C | 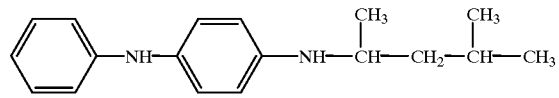 |
| IH | 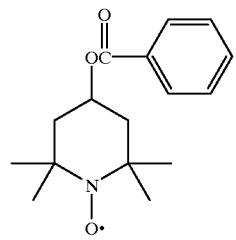 |
| MTX | 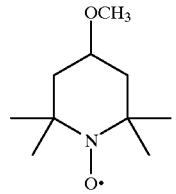 |

The α,β-unsaturated carboxylic acids and esters thereof which were used therein are designated by the following abbreviations.

CHMA: Cyclohexyl methacrylate
EDMA: Ethylene glycol dimethacrylate
BMA: n-Butyl methacrylate
BZMA: Benzyl methacrylate
EHMA: 2-Ethylhexyl methacrylate
AMA: Allyl methacrylate
HEMA: 2-Hydroxyethyl methacrylate
GMA: Glycidyl methacrylate
HEA: 2-Hydroxyethyl acrylate
MA: Methyl acrylate
MMA: Methyl methacrylate
AA: Acrylic acid
MAA: Methacrylic acid

EXAMPLE 1

A four-necked flask fitted with a stirrer, a thermometer and a brine condenser was charged with 4-hydroxy-2,2,6,6-tetramethylpiperidine-N-oxyl as a starting material, toluene and iron(III) chloride. While this mixture was being stirred, ethylene oxide was blown thereinto to effect an addition reaction at a reaction temperature of 10–15° C. The blowing rate of ethylene oxide was such that it was not refluxed in the lower part of the brine condenser. After ethylene oxide was blown in until its molar amount added became equal to six times that of 4-hydroxy-2,2,6,6-tetramethylpiperidine-N-oxyl charged, the stirring was continued. After the disappearance of 4-hydroxy-2,2,6,6-tetramethylpiperidine-N-oxyl was confirmed through analysis by high-performance liquid chromatography, the reaction was stopped. Thereafter, the reaction mixture was stirred under reduced pressure to remove any unreacted ethylene oxide, and then washed with water to remove any 4-hydroxy-2,2,6,6-tetramethylpiperidine-N-oxyl and the catalyst. Finally, the toluene was removed under reduced pressure to obtain IB shown in Table 1. The results of analysis of IB by high-performance liquid chromatography are shown in FIG. 1. The conditions employed for analysis by high-performance liquid chromatography were as follows.
Measuring Conditions of High-performance Liquid Chromatography
  Apparatus: Shimadzu LC-6A
  Column: Inertsil ODS-80A, 4.6 mm$\phi$×250 mm
  Mobile phase: $CH_3CN/H_2O/H_3PO_4$=400/600/1
  Flow velocity: 1.0 ml/min
  Temperature: 40° C.
  Detection: UV 240 nm (ABS 0.02)
  Moreover, IA and IC were prepared in the same manner as described for IB, except that the amount of ethylene oxide blown in was varied.

EXAMPLE 2

Figure 2:
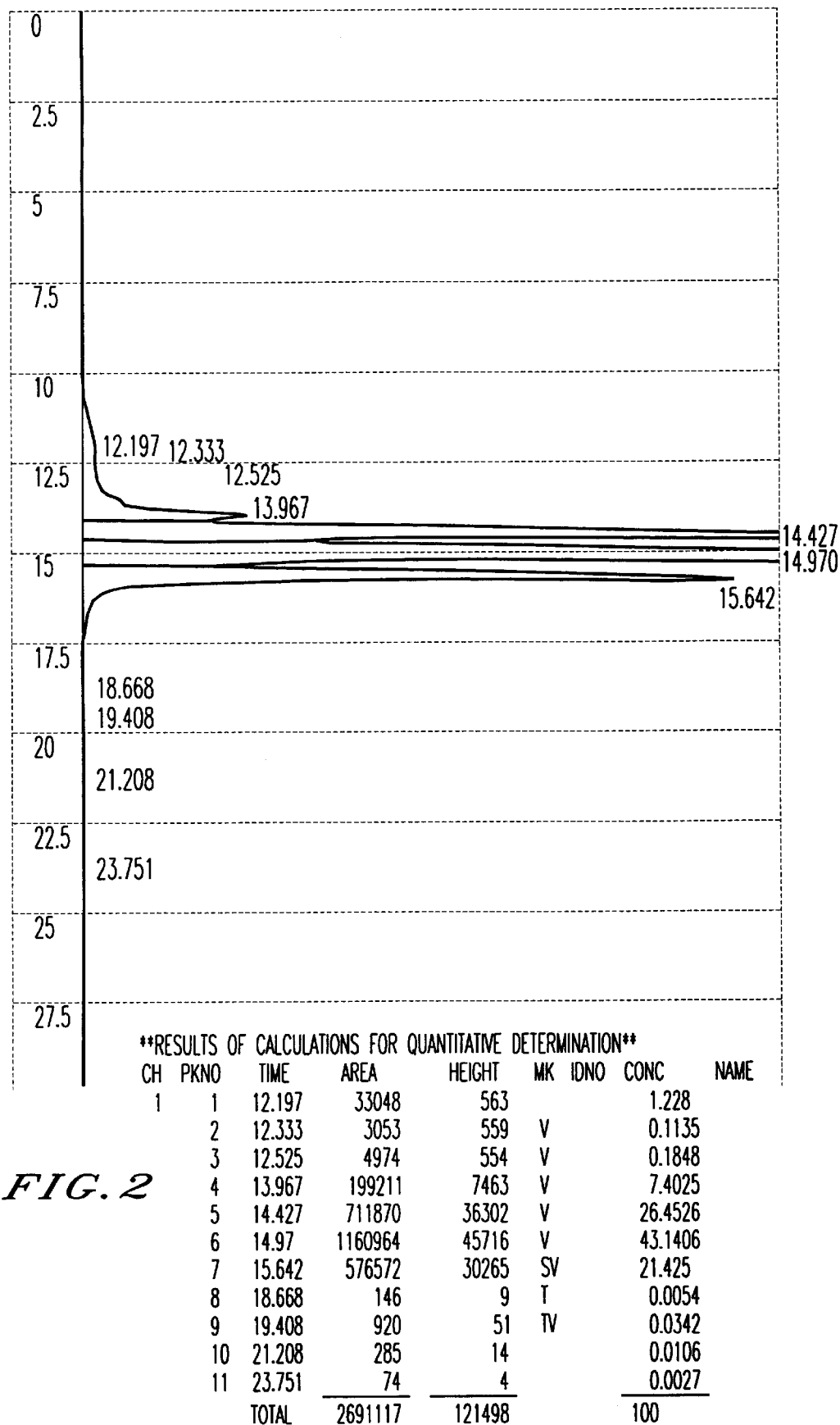

A four-necked flask fitted with a stirrer, a thermometer and a brine condenser was charged with 4-hydroxy-2,2,6,6-tetramethylpiperidine-N-oxyl as a starting material, toluene and iron(III) chloride. While this mixture was being stirred, propylene oxide was dropped thereinto to effect an addition reaction at a reaction temperature of 15–20° C. The dropping rate of propylene oxide was such that it was not refluxed in the lower part of the brine condenser. After propylene oxide was dropped until its molar amount added became equal to three times that of 4-hydroxy-2,2,6,6-tetramethylpiperidine-N-oxyl charged, the stirring was continued. After the disappearance of 4-hydroxy-2,2,6,6-tetramethylpiperidine-N-oxyl was confirmed through analysis by high-performance liquid chromatography, the reaction was stopped. Thereafter, the reaction mixture was stirred under reduced pressure to remove any unreacted propylene oxide, and then washed with water to remove any 4-hydroxy-2,2,6,6-tetramethylpiperidine-N-oxyl and the catalyst. Finally, the toluene was removed under reduced pressure to obtain IE shown in Table 1. The results of analysis of IE by high-performance liquid chromatography are shown in FIG. 2. The conditions employed for analysis by high-performance liquid chromatography were the same as for IA.

Moreover, IF and IG were prepared in the same manner as described for IE, except that the amount of propylene oxide blown in was varied.

EXAMPLES 3–8 AND COMPARATIVE EXAMPLES 1–5

Test solutions were prepared by adding 5 ppm of each polymerization inhibitor to the various (meth)acrylic esters shown in Table 3 and from which any polymerization inhibitor had previously been removed by distillation. Then, 15 g each of the aforesaid test solutions were poured into 25 ml ampules. These ampules were sealed with silicone stoppers and immersed in an oil bath kept at 70° C. for methyl acrylate (MA), 90° C. for methyl methacrylate (MMA), or 120° C. for other (meth)acrylic esters. While this oil bath was being shaken on a shaker, the ampules were visually observed to confirm the time at which popcorn formation, gelation or an increase in solution viscosity occurred. Thus, the polymerization initiation time (in minutes) of the (meth) acrylic ester in each ampule was determined. The results thus obtained are also shown in Table 3.

TABLE 3

| No. | Polymerization inhibitor | Polymerization initiation time (min.) | | | | | | | | | | |
|---|---|---|---|---|---|---|---|---|---|---|---|---|
| | | CHMA | EDMA | BMA | AMA | HEMA | GMA | EHMA | BZMA | HEA | MA | MMA |
| Example 3 | IA | 849 | 993 | 1001 | >1100 | 713 | 815 | 1054 | 1035 | 630 | >1100 | >1100 |
| Example 4 | IB | 519 | 598 | 608 | 681 | 449 | 503 | 666 | 639 | 674 | >1100 | 880 |
| Example 5 | IC | 376 | 420 | 451 | 505 | 328 | 340 | 490 | 421 | 380 | 758 | 667 |
| Example 6 | IE | 653 | 751 | 778 | 876 | 553 | 610 | 838 | 767 | 495 | >1100 | >1100 |
| Example 7 | IF | 433 | 500 | 525 | 588 | 379 | 439 | 560 | 530 | 357 | 889 | 734 |
| Example 8 | IG | 304 | 333 | 365 | 408 | 258 | 288 | 390 | 338 | 274 | 590 | 503 |
| Comparative Example 1 | PZ | 57 | 31 | 50 | 42 | 40 | 48 | 70 | 60 | 35 | 126 | 112 |
| Comparative Example 2 | HQ | 60 | 31 | 52 | 43 | 41 | 51 | 75 | 64 | 41 | 124 | 120 |
| Comparative Example 3 | MEHQ | 12 | 5 | 10 | 7 | 9 | 10 | 13 | 13 | 11 | 47 | 38 |
| Comparative Example 4 | AF | 43 | 21 | 37 | 30 | 31 | 35 | 54 | 46 | 30 | 120 | 106 |
| Comparative Example 5 | 6C | 23 | 5 | 19 | 15 | 13 | 15 | 30 | 27 | 14 | 63 | 60 |

EXAMPLES 9–14 AND COMPARATIVE EXAMPLES 6–10

Test solutions were prepared by adding 5 ppm of each of the polymerization inhibitors shown in Table 4 to (meth) acrylic acid from which any polymerization inhibitor had previously been removed by distillation. Then, 15 g each of the aforesaid test solutions were poured into 25 ml ampules. These ampules were sealed with silicone stoppers and immersed in an oil bath kept at 100° C. While this oil bath was being shaken on a shaker, the ampules were visually observed to confirm the time at which popcorn formation, gelation or an increase in solution viscosity occurred. Thus, the polymerization initiation time (in minutes) of (meth) acrylic acid in each ampule was determined. The results thus obtained are also shown in Table 4.

TABLE 4

| Example No. | Polymerization inhibitor | Polymerization initiation time (min.) Acrylic acid | Polymerization initiation time (min.) Methacrylic acid |
|---|---|---|---|
| Example 9 | IA | 77 | 126 |
| Example 10 | IB | 40 | 79 |
| Example 11 | IC | 28 | 51 |
| Example 12 | IE | 58 | 94 |
| Example 13 | IF | 36 | 64 |
| Example 14 | IG | 25 | 43 |
| Comparative Example 6 | Pz | 8 | 16 |
| Comparative Example 7 | HQ | 1 | 2 |
| Comparative Example 8 | MEHQ | 2 | 4 |
| Comparative Example 9 | AF | 7 | 14 |
| Comparative Example 10 | 6C | 3 | 6 |

It can be seen from Tables 3 and 4 that, when the N-oxyl compounds of the above formula (1) were used as polymerization inhibitors, the polymerization initiation time of α,β-unsaturated carboxylic acids and esters thereof was markedly prolonged to exhibit a more excellent polymerization-inhibiting effect, as compared with the cases in which conventional polymerization inhibitors such as phenothiazine, hydroquinone, hydroquinone monomethyl ether, AF, and 6C were used.

EXAMPLES 15–19 AND COMPARATIVE EXAMPLES 11–14

Test solutions were prepared by adding each of the polymerization inhibitors shown in Table 5 to ethylene glycol dimethacrylate from which any polymerization inhibitor had previously been removed by distillation. Then, 15 g each of the aforesaid test solutions were poured into 25 ml ampules. These ampules were sealed with silicone stoppers and immersed in an oil bath kept at 120° C. While this oil bath was being shaken on a shaker, the ampules were visually observed to determine the polymerization initiation time (in minutes) of ethylene glycol dimethacrylate in each ampule. The results thus obtained are also shown in Table 5.

TABLE 5

| No. | Polymerization inhibitor | Amount added (ppm) | Polymerization initiation time (min.) |
|---|---|---|---|
| Example 15 | IB | 3 | 159 |
| Example 16 | IB | 3 | 195 |
|  | MEHQ | 10 |  |
| Example 17 | IB | 3 | 228 |
|  | HQ | 10 |  |
| Example 18 | IB | 3 | 210 |
|  | AF | 10 |  |
| Example 19 | IB | 3 | 199 |
|  | 6C | 10 |  |
| Comparative Example 11 | MEHQ | 10 | 10 |
| Comparative Example 12 | HQ | 10 | 66 |
| Comparative Example 13 | AF | 10 | 46 |
| Comparative Example 14 | 6C | 10 | 10 |

It can be seen from Table 5 that the polymerization-inhibiting effect of the N-oxyl compounds of the above formula (1) was further enhanced by the combined use of other general-purpose polymerization inhibitors.

EXAMPLE 20

Using a reflux apparatus equipped with a 20-plates Oldershaw column as the distillation column, a 3-liter four-necked flask with a side arm was charged with 2,002 g (20 moles) of methyl methacrylate, 248 g (4 moles) of ethylene glycol, 14.4 g of dibutyltin oxide, and 0.79 g (corresponding to 0.1% of the theoretical yield of the product) of IB as a polymerization inhibitor. This mixture was subjected to an ester exchange reaction. The methanol formed as a by-product during reaction was removed from the system together with the methyl methacrylate. The resulting reaction product was purified by simple distillation using an empty column having a length of 20 cm, so that 530 g of ethylene glycol dimethacrylate was obtained. During the course of the reaction and distillation, polymerization occurred neither in the reactor nor the column. The ethylene glycol dimethacrylate thus obtained had a color number (APHA) of not greater than 5.

COMPARATIVE EXAMPLE 15

Ethylene glycol dimethacrylate was synthesized in the same manner as in Example 20, except that the polymerization inhibitor used was changed from IB to ID. During the course of the reaction and distillation, polymerization occurred neither in the reactor nor the column. However, the ethylene glycol dimethacrylate thus obtained had a color number (APHA) of 35.

COMPARATIVE EXAMPLE 16

Ethylene glycol dimethacrylate was synthesized in the same manner as in Example 20, except that the polymerization inhibitor used was changed from IB to IH. During the course of the reaction and distillation, polymerization occurred neither in the reactor nor the column. However, the ethylene glycol dimethacrylate product had a color number (APHA) of 20.

COMPARATIVE EXAMPLE 17

Ethylene glycol dimethacrylate was synthesized in the same manner as in Example 20, except that the polymerization inhibitor used was changed from IB to AF. However, polymerization occurred in the reactor during the course of the distillation step.

EXAMPLE 21

Using a reflux apparatus equipped with a 20-plates Oldershaw column as the distillation column, a 3-liter four-necked flask with a side arm was charged with 1,401 g (14 moles) of methyl methacrylate, 701 g (7 moles) of cyclohexanol, 12.6 g of dibutyltin oxide, and 1.18 g (corresponding to 0.1% of the theoretical yield of the product) of IB as a polymerization inhibitor. This mixture was subjected to an ester exchange reaction. The methanol formed as a by-product during reaction was removed from the system together with the methyl methacrylate. The resulting reaction product was purified by simple distillation using an empty column having a length of 20 cm, so that 740 g of cyclohexyl methacrylate was obtained. During the course of the reaction and distillation, polymerization occurred neither in the reactor nor the column. The cyclohexyl methacrylate thus obtained had a color number (APHA) of not greater than 5.

COMPARATIVE EXAMPLE 18

Using a reflux apparatus equipped with a 20-plates Oldershaw column as the distillation column, a 3-liter four-necked flask with a side arm was charged with 1,401 g (14 moles) of methyl methacrylate, 701 g (7 moles) of cyclohexanol, 12.6 g of dibutyltin oxide, and 1.18 g (corresponding to 0.1% of the theoretical yield of the product) of MTX as a polymerization inhibitor. This mixture was subjected to an ester exchange reaction. The methanol formed as a by-product during reaction was removed from the system together with the methyl methacrylate. The resulting reaction product was purified by simple distillation using an empty column having a length of 20 cm, so that 848 g of cyclohexyl methacrylate was obtained. During the course of the reaction and distillation, polymerization occurred neither in the reactor nor the column. However, the cyclohexyl methacrylate thus obtained was slightly colored and had a color number (APHA) of 140.

EXPLOITABILITY IN INDUSTRY

When the N-oxyl compounds represented by the above formula (1) are used as polymerization inhibitors by adding them to vinyl monomers in small amounts, a satisfactory polymerization-inhibiting effect is obtained at high temperatures. Moreover, when they are used as process inhibitors, especially in the purification of α,β-unsaturated carboxylic acids and esters thereof by distillation, they are not distilled out together with the product and hence cause no coloration thereof. Thus, they can be used as process inhibitors for vinyl monomers having high boiling points, without causing any trouble. This contributes greatly to the stable production of vinyl monomers, particularly α,β-unsaturated carboxylic acids and esters thereof.

We claim:

1. An N-oxyl compound of the following formula (1):

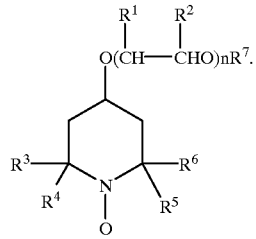

(1)

wherein n is an integer of 2 to 9; $R^1$ and $R^2$ are each hydrogen or methyl, but at least one of them is hydrogen;

$R^3$, $R^4$, $R^5$ and $R^6$ are each a straight-chain or branched alkyl group; and $R^7$ is hydrogen or (meth)acryloyl.

2. A mixture of N-oxyl compounds which comprises two or more N-oxyl compounds of the following formula (1) having different values of n:

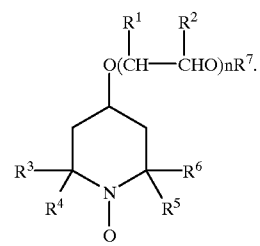

(2)

wherein n is an integer of 1 to 18; $R^1$ and $R^2$ are each hydrogen or methyl, but at least one of them is hydrogen; $R^3$, $R^4$, $R^5$ and $R^6$ are each a straight-chain or branched alkyl group; and $R^7$ is hydrogen or (meth)acryloyl.

3. A process for the preparation of an N-oxyl compound as claimed in claim 1 which comprises effecting the addition of ethylene oxide and/or propylene oxide to a 4-hydroxy-2,2,6,6-tetraalkylpiperidine-N-oxyl, and optionally esterifying the resulting product with a (meth)acryloyl-containing compound.

4. A polymerization inhibition method wherein an N-oxyl compound as claimed in claim 1 is used as a polymerization inhibitor for vinyl monomers.

5. The polymerization inhibition method as claimed in claim 4 wherein the vinyl monomers are α,β-unsaturated carboxylic acids and esters thereof.

6. A polymerization inhibition method wherein the N-oxyl compound prepared according to the process of claim 3 is used as a polymerization inhibitor for vinyl monomers.

7. A polymerization inhibition method as claimed in claim 6 wherein the vinyl monomers are α,β-unsaturated carboxylic acids and esters thereof.

8. A process for the preparation of the mixture of N-oxyl compounds as claimed in claim 2, which comprises effecting the addition of ethylene oxide and/or propylene oxide to a 4-hydroxy-2,2,6,6-tetraalkylpiperidine-N-oxyl, and optionally esterifying the resulting product with a (meth)acryloyl-containing compound.

9. A polymerization inhibition method wherein the mixture of N-oxyl compounds as claimed in claim 2 is used as a polymerization inhibitor for vinyl monomers.

10. The polymerization inhibition method as claimed in claim 9, wherein the vinyl monomers are α,β-unsaturated carboxylic acids and esters thereof.

11. A polymerization inhibition method wherein the mixture of N-oxyl compounds prepared according to the process of claim 8 is used as a polymerization inhibitor for vinyl monomers.

12. The polymerization inhibition method as claimed in claim 11, wherein the vinyl monomers are α,β-unsaturated carboxylic acids and esters thereof.

* * * * *

UNITED STATES PATENT AND TRADEMARK OFFICE
CERTIFICATE OF CORRECTION

PATENT NO. : 6,348,598 B1  
DATED : February 19, 2002  
INVENTOR(S) : Doi et al.

It is certified that error appears in the above-identified patent and that said Letters Patent is hereby corrected as shown below:

<u>Title page,</u>
Item [30], the Foreign Application Priority information should read:

-- [30]     Foreign Application Priority Data  
    Nov. 12, 1997  (JP) ....................................... 9-310573 --

Signed and Sealed this

Third Day of September, 2002

*Attest:*

*Attesting Officer*

JAMES E. ROGAN  
*Director of the United States Patent and Trademark Office*